United States Patent
Nakanishi et al.

(10) Patent No.: US 7,848,480 B2
(45) Date of Patent: Dec. 7, 2010

(54) X-RAY CT SCANNER AND DATA PROCESSING METHOD OF X-RAY CT SCANNER

(75) Inventors: Satoru Nakanishi, Utsunomiya (JP); Naruomi Akino, Nasushiobara (JP); Yasuo Saito, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 531 days.

(21) Appl. No.: 11/776,866

(22) Filed: Jul. 12, 2007

(65) Prior Publication Data
US 2008/0019474 A1    Jan. 24, 2008

(30) Foreign Application Priority Data
Jul. 19, 2006   (JP) .............................. 2006-197147
Jun. 29, 2007   (JP) .............................. 2007-172196

(51) Int. Cl.
*A61B 6/03* (2006.01)
(52) U.S. Cl. ............................................. 378/9; 378/4
(58) Field of Classification Search ............... 378/4, 378/9
See application file for complete search history.

(56) References Cited

U.S. PATENT DOCUMENTS

| 5,528,644 | A  * | 6/1996 | Ogawa et al. ................. 378/8 |
| 6,421,412 | B1   | 7/2002 | Hsieh et al. |
| 6,445,761 | B1 * | 9/2002 | Miyazaki et al. .............. 378/8 |
| 2004/0114706 | A1   | 6/2004 | Ikeda et al. |
| 2005/0089134 | A1   | 4/2005 | Bruder et al. |
| 2005/0175143 | A1   | 8/2005 | Miyazaki et al. |
| 2006/0045235 | A1 * | 3/2006 | Bruder et al. ................. 378/9 |

(Continued)

FOREIGN PATENT DOCUMENTS

CN          1517072 A       8/2004

(Continued)

OTHER PUBLICATIONS

Bruder et al., Design considerations in cardiac CT, Feb. 28, 2006, SPIE, Medical Imaging 2006: Physics of Medical Imaging, vol. 6142, pp. 61420H-1-61420H-13.*

*Primary Examiner*—Edward J Glick
*Assistant Examiner*—John M Corbett
(74) *Attorney, Agent, or Firm*—Oblon, Spivak, McClelland, Maier & Neustadt, L.L.P.

(57) ABSTRACT

An X-ray CT scanner includes X-ray tubes including a first X-ray tube and a second X-ray tube having fan angles different from each other, X-ray detectors including a first X-ray detector and a second X-ray detector which are respectively arranged to face the first X-ray tube and the second X-ray tube, collection data processing means for executing weighting processing to each of pieces of collection data including first collection data obtained by the first X-ray detector and second collection data obtained by the second X-ray detector to generate image data combined to be smooth in a direction corresponding to a channel direction of detection elements provided in the X-ray detectors, and image generating section for performing processing including image reconstruction processing with respect to pieces of collection data weighted by the collection data processing section to generate image data.

8 Claims, 10 Drawing Sheets

U.S. PATENT DOCUMENTS

2006/0193430 A1* 8/2006 Kuhn ........................... 378/9
2007/0025499 A1* 2/2007 Bruder et al. ................. 378/9

FOREIGN PATENT DOCUMENTS

| | | | |
|---|---|---|---|
| CN | 1658796 A | | 8/2005 |
| CN | 1762305 A | | 4/2006 |
| DE | 10354214 A1 | * | 6/2005 |
| DE | 10354900 A1 | * | 6/2005 |
| EP | 0 599 207 A2 | | 6/1994 |
| JP | 5-168616 | | 7/1993 |
| JP | 2001-346791 | | 12/2001 |
| JP | 2005185312 A | * | 7/2005 |
| WO | WO 98/32371 | | 7/1998 |
| WO | WO 2005004722 A2 | * | 1/2005 |

* cited by examiner

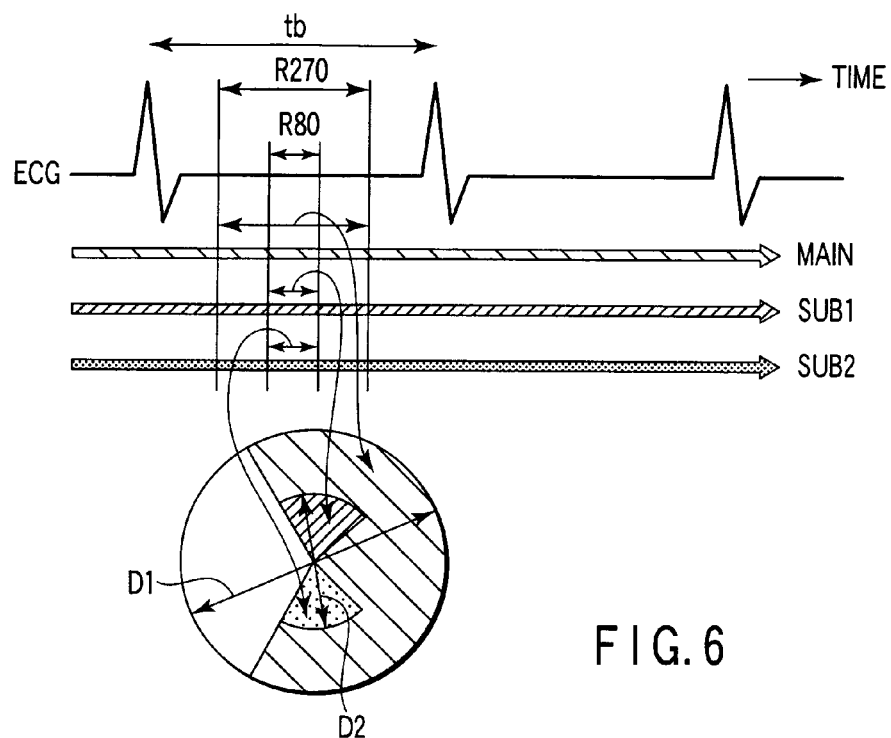
F I G. 6
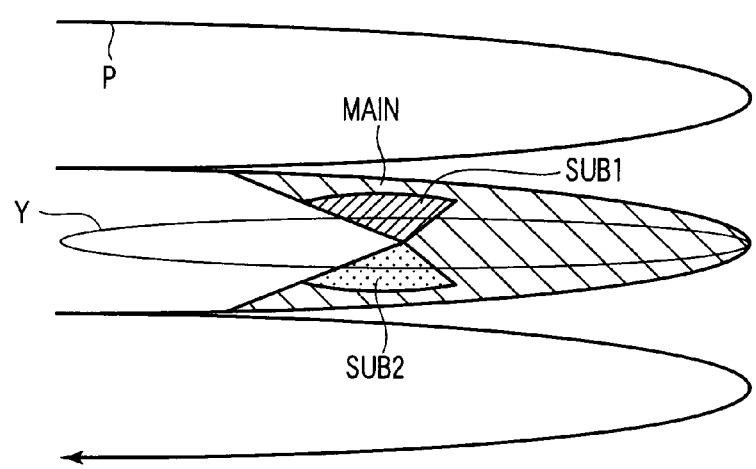
F I G. 7

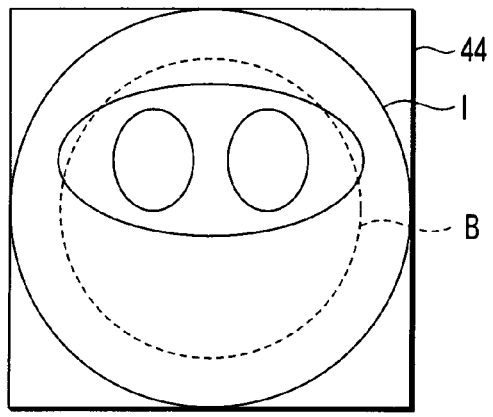
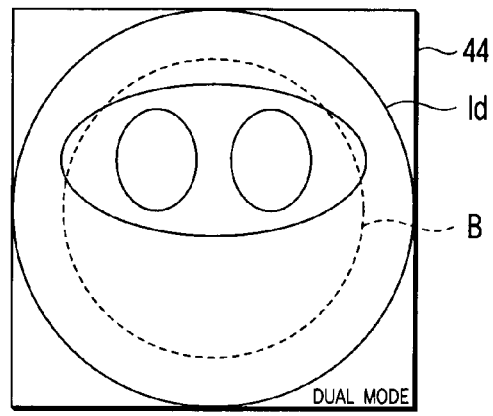
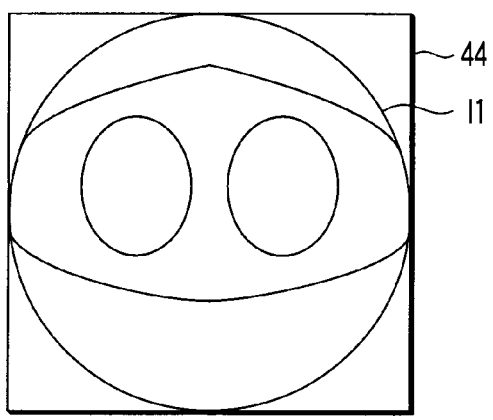
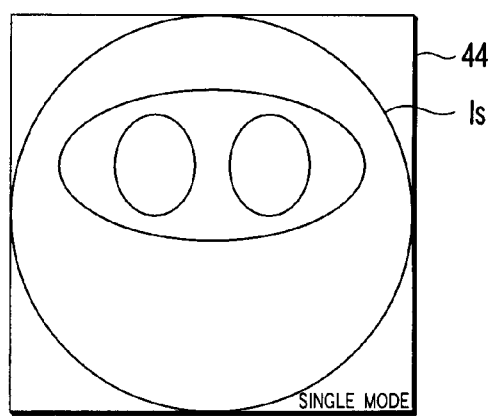
FIG. 11
FIG. 12

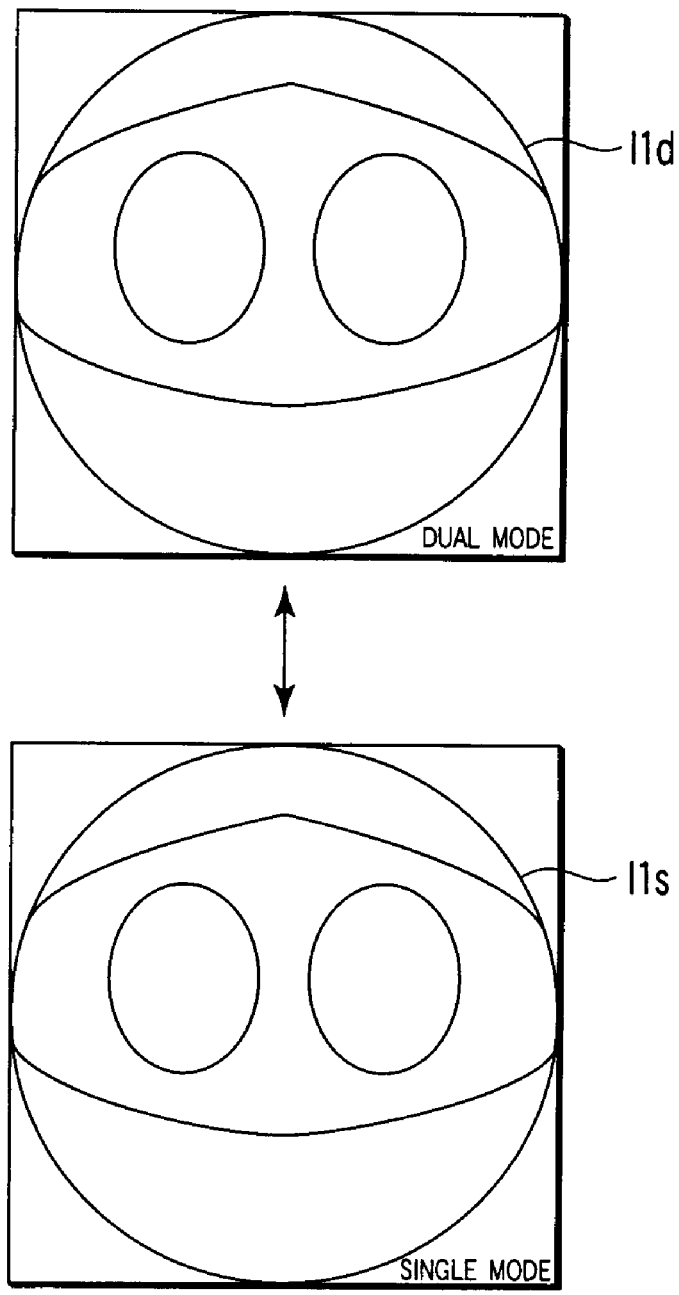
F I G. 13

X-RAY CT SCANNER AND DATA PROCESSING METHOD OF X-RAY CT SCANNER

CROSS-REFERENCE TO RELATED APPLICATIONS

This application is based upon and claims the benefit of priority from prior Japanese Patent Applications No. 2006-197147, filed Jul. 19, 2006; and No. 2007-172196, filed Jun. 29, 2007, the entire contents of both of which are incorporated herein by reference.

BACKGROUND OF THE INVENTION

1. Field of the Invention

The present invention relates to an X-ray computed tomography (CT) scanner that reconstructs a diagnostic image of a subject from X-ray detection data collected by irradiating the subject with an X-ray and a data processing method of the X-ray CT scanner, and more particularly to an X-ray CT scanner including a plurality of bulbs and a data processing method of the X-ray CT scanner.

2. Description of the Related Art

An X-ray CT scanner is an apparatus that irradiates a subject with an X-ray from a bulb of an X-ray tube and performs image reconstruction processing with respect to X-ray detection data collected by an X-ray detector to reconstruct a diagnostic image of the subject. As one of diagnostic image reconstruction techniques using this X-ray CT scanner, there is half reconstruction. According to the half reconstruction, projection data of an angle less than 360 degrees (generally, projection data of 180 degrees+a fan angle) is used and one image is thereby generated to reconstruct a diagnostic image, whereas data corresponding to a direction of 360 degrees is detected with respect to a subject to reconstruct a diagnostic image in regular image reconstruction processing.

This half reconstruction technology can reconstruct an image from projection data in a small angle range and can obtain an image with a high time resolution, and hence it is often used to obtain an image of a part having a local movement, e.g., the heart. In particular, an image with less influence of a movement can be obtained by obtaining an image of the heart based on half reconstruction of X-ray detection data of an angle less than 360 degrees collected based on electrocardiographic synchronization.

FIG. 1 is a conceptual view for explaining a method of collecting half reconstruction data based on electrocardiographic synchronization using a conventional X-ray CT scanner.

As shown in FIG. 1, in a beat period of an ECT (Electrocardiogram) signal, a subject is irradiated with an X-ray from a bulb #1, and half data Dh is collected by an X-ray detector. Further, the half data Dh depicted in FIG. 1 is data corresponding to approximately 210 to 240 degrees, e.g., approximately 240 degrees.

However, when the number of beats per minute is 120, since a time tb of one heartbeat is 0.5 s, a comparable time resolution is required when collecting data in one heartbeat. However, collecting sufficient half data is usually difficult in one heartbeat in many cases, and a technique of dividing data into segments over a plurality of heartbeats to collect half data has been proposed.

FIG. 2 is a conceptual view for explaining a technique of dividing half reconstruction data into segments based on eletrocardiographic synchronization to collect the data by using a conventional X-ray CT scanner.

As indicated by a bulb trajectory P in FIG. 2, a technique of helically moving the bulb around a subject and collecting one segment S1 of half data in a first cardiac beam B1 and two segments S2 and 3 of the half data in second and third heartbeats B2 and B3 has been proposed. Furthermore, the half data of approximately 240 degrees in a reconstruction plane Y can be obtained based on data collection in the three heartbeats.

On the other hand, a multi-bulb X-ray CT scanner has been designed as an attempt to improve a time resolution. The multi-bulb X-ray CT scanner is an apparatus having a structure where a plurality of bulbs are provided in the X-ray CT scanner and an X-ray detector arranged to face each bulb detects an X-ray applied to a subject from each bulb.

In this multi-bulb X-ray CT scanner, a three-bulb X-ray CT scanner including three bulbs has been designed in particular. In case of the three-bulb X-ray CT scanner, an apparatus in which pairs of three bulbs and three detectors are uniformly arranged at 120 degrees has been designed (see, e.g., JP-A 168616-1993 [KOKAI] and JP-A 2001-346791 [KOKAI]). When collecting data corresponding to 360 degrees, using this three-bulb X-ray CT scanner enables collecting the data corresponding to 360 degrees with a rotating angle of 120 degrees. Therefore, as compared with the X-ray CT scanner having one bulb, it can be expected that data can be ideally collected in a time reduced to ⅓.

FIG. 3 is a conceptual view for explaining a technique when collecting data by using the conventionally designed three-bulb X-ray CT scanner.

As shown in a state St01 in FIG. 3, when three bulbs #1, #2, and #3 are equally arranged at angle intervals of 120 degrees, a state St02 is obtained by rotating each of the bulbs #1, #2, and #3 at 120 degrees, thereby collecting data corresponding to 360 degrees.

Therefore, when a rotating speed of each bulb is 0.3 s/rotation, a time required to collect the data corresponding to 360 degrees is 120/360×0.3=0.1 s, which is ⅓ of that in an example where one bulb is used.

FIG. 4 is a conceptual view showing data collected by the conventionally designed three-bulb X-ray CT scanner.

In FIG. 4, an ordinate represents a data collection range expressed as an irradiation angle of an X-ray with respect to a subject, and an abscissa represents a channel (Ch) used by each X-ray detector. As shown in FIG. 4, each X-ray detector facing each of three bulbs #1, #2, and #3 collects data corresponding to 120 degrees in each different region. Furthermore, the number of channels of a detection element provided in each X-ray detector is the same, and X-rays are detected in all the channels.

As a result, as shown in FIG. 4, each X-ray detector collects data D#1', D#2', and D#3' each corresponding to 120 degrees in accordance with the number of channels, the number of pieces of data being the same in the respective detectors. That is, the three-bulb X-ray CT scanner collects data corresponding to 360 degrees that is in proportion to the number of channels.

Moreover, it is considered that the multi-bulb X-ray CT scanner is effective for high-speed scanning in terms of such a time resolution.

In imaging using the X-ray CT scanner, as explained above, an improvement in a time resolution is an important problem. Thus, utilization of the multi-bulb X-ray scanner is expected for data collection requiring a time resolution. However, an irradiation amount of X-rays is increased when the number of bulbs is increased, and hence an exposure amount of a subject grows. Additionally, when the number of bulbs is increased, a size of each X-ray detector is increased, thus pushing up a manufacturing cost.

In general, a time resolution is required when an imaging field of view (FOV) is mainly narrow and an image of a local region, e.g., the heart is imaged in particular. Thus, when a fan angle of an X-ray tube and a size of each X-ray detector are reduced, imaging in a wide region with a relatively low time resolution becomes difficult. That is, when reducing the size of the X-ray detector to assure a high time resolution with a smaller irradiation amount of X-rays, assuring a sufficiently wide FOV is difficult.

Further, when the multi-bulb X-ray CT scanner in which bulbs having the same size are evenly arranged is used, 360-degree rotation according to the number of the bulbs does not have to be carried out, and a time resolution can be improved as compared with an example where the X-ray CT scanner having a single bulb is used to perform full reconstruction. However, in order to collect data that is continuous in terms of angles, full reconstruction must be carried out, and using the half reconstruction technology is difficult. Therefore, when capturing an image of a local region, a further improvement in a time resolution is demanded.

BRIEF SUMMARY OF THE INVENTION

Therefore, it is an object of the present invention to provide an X-ray CT scanner and a data processing method of the X-ray CT scanner that can irradiate a subject with an X-ray having a smaller irradiation amount from a plurality of bulbs to capture an image with a time resolution and an FOV meeting a diagnostic purpose.

An object of the present invention is to provide an X-ray CT scanner comprising:

a plurality of X-ray tubes including a first X-ray tube and a second X-ray tube having fan angles different from each other;

a plurality of X-ray detectors which are respectively arranged to face the first X-ray tube and the second X-ray tube and include a first X-ray detector and a second X-ray detector having detection elements;

a collection data processing section which smoothly executes weighting processing with respect to a plurality of pieces of collection data including first collection data obtained by the first X-ray detector and second collection data obtained by the second X-ray detector in a direction corresponding to a channel direction of the detection elements of the plurality of X-ray detectors; and a first image generating section which performs image reconstruction processing with respect to the plurality of pieces of collection data weighted by the collection data processing section to generate image data.

Furthermore, another object of the present invention is to provide a data processing method of an X-ray CT scanner, comprising:

a first step of acquiring a plurality of pieces of collection data including first collection data and second collection data which are respectively emitted from a plurality of X-ray tubes including a first X-ray tube and a second X-ray tube having fan angles different from each other and respectively obtained by a first X-ray detector and a second X-ray detector which are respectively arranged to face the first X-ray tube and the second X-ray tube and have detection elements;

a second step of executing weighting processing with respect to each of the plurality of pieces of collection data to generate image data combined to be smooth in a direction corresponding to a channel direction of the detection elements in the first X-ray detector and the second X-ray detector; and a third step of performing processing including image reconstruction processing with respect to the plurality of pieces of weighted collection data to generate the image data.

In the X-ray CT scanner and the data processing method of the X-ray CT scanner according to the present invention, a subject is irradiated with X-rays having a smaller irradiation amount from the plurality of bulbs, and an image can be captured with a time resolution and an FOV meeting a diagnostic purpose.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a conceptual view for explaining a method of detecting data for half reconstruction by three X-ray detectors in synchronization with an ECG signal by using the X-ray CT scanner depicted in FIG. 5;

FIG. 7 is another conceptual view for explaining a method of detecting data for half reconstruction by the three X-ray detectors in synchronization with the ECG signal by using the X-ray CT scanner depicted in FIG. 5;

FIG. 11 is a view showing an example where image data I1 in the local FOV alone is displayed in the display device depicted in FIG. 5 in an enlarging manner in accordance with a size of the image data I in the wide FOV;

FIG. 12 is a view showing an example where image data in the wide FOV reconstructed in a single mode and image data in the wide FOV reconstructed in a dual mode are switched and displayed in the display device depicted in FIG. 5;

FIG. 13 is a view showing an example where image data in the local FOV reconstructed in the single mode and image data in the local FOV reconstructed in the dual mode are switched and displayed in the display device depicted in FIG. 5;

DETAILED DESCRIPTION OF THE INVENTION

Embodiments of an X-ray CT scanner and a data processing method of the X-ray CT scanner according to the present invention will now be explained hereinafter with reference to the accompanying drawings.

First Embodiment

Figure 1:
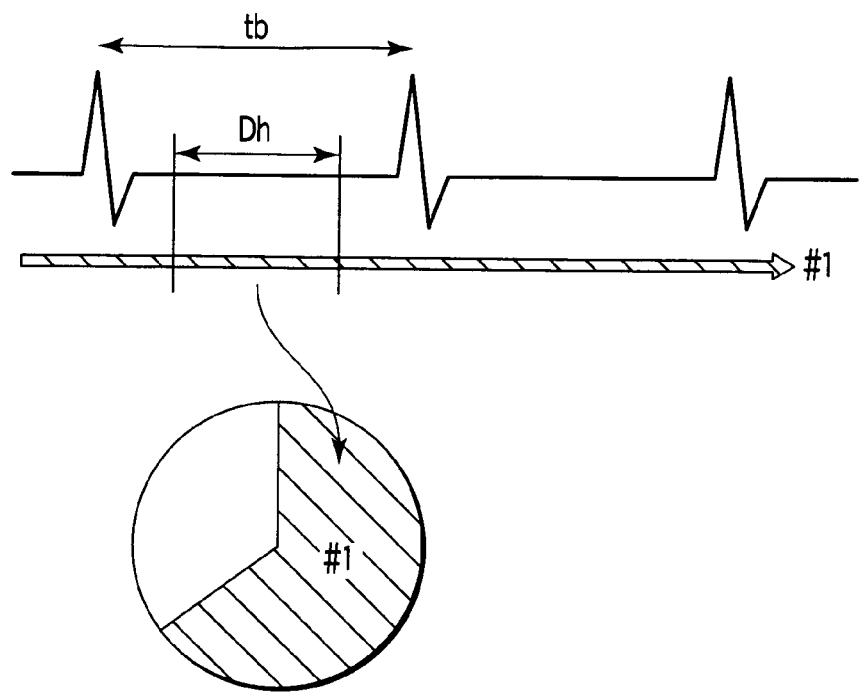
FIG. 1 is a conceptual view for explaining a method of collecting data for half reconstruction based on electrocardiographic synchronization using a conventional X-ray CT scanner.
Figure 2:
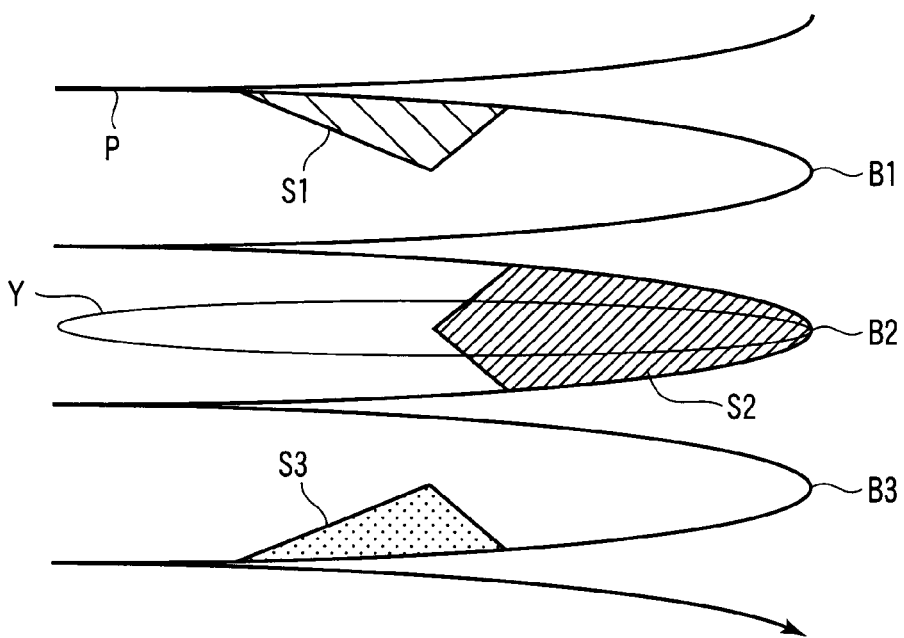
FIG. 2 is a conceptual view for explaining a technique of dividing data for half reconstruction into segments and collecting the divided data based on electrocardiographic synchronization using the conventional X-ray CT scanner.
Figure 3:
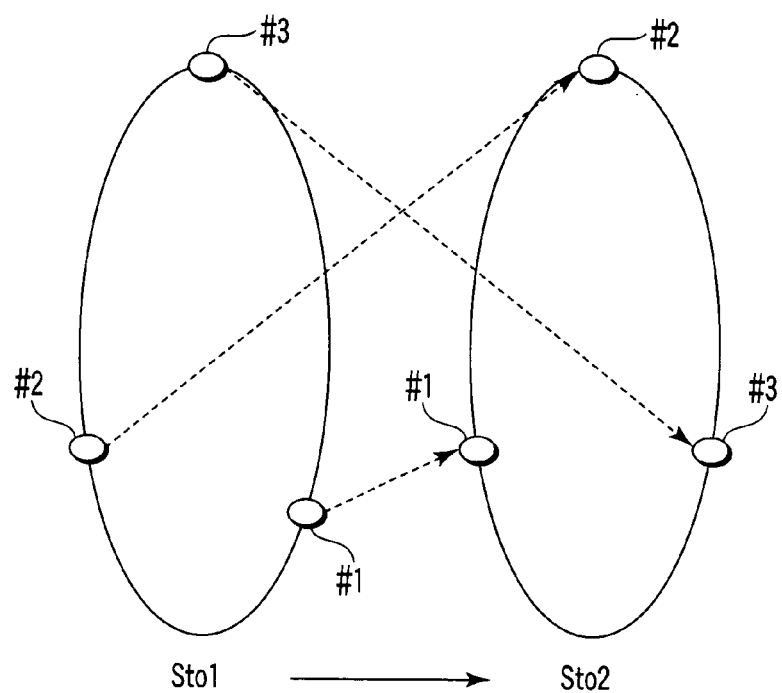
FIG. 3 is a conceptual view for explaining a technique of collecting data by a conventionally designed three-bulb X-ray CT scanner.
Figure 4:
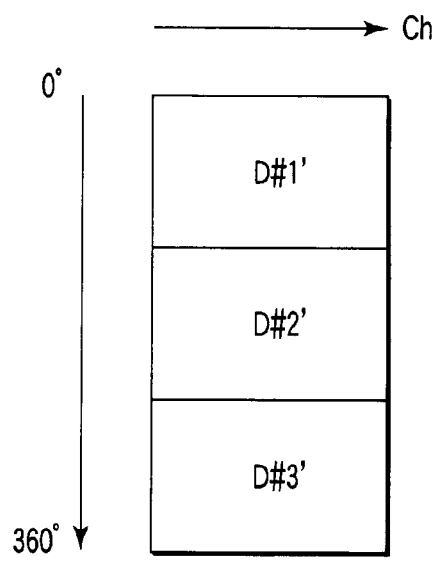
FIG. 4 is a conceptual view showing data collected by the conventionally designed three-bulb X-ray CT scanner.
Figure 5:
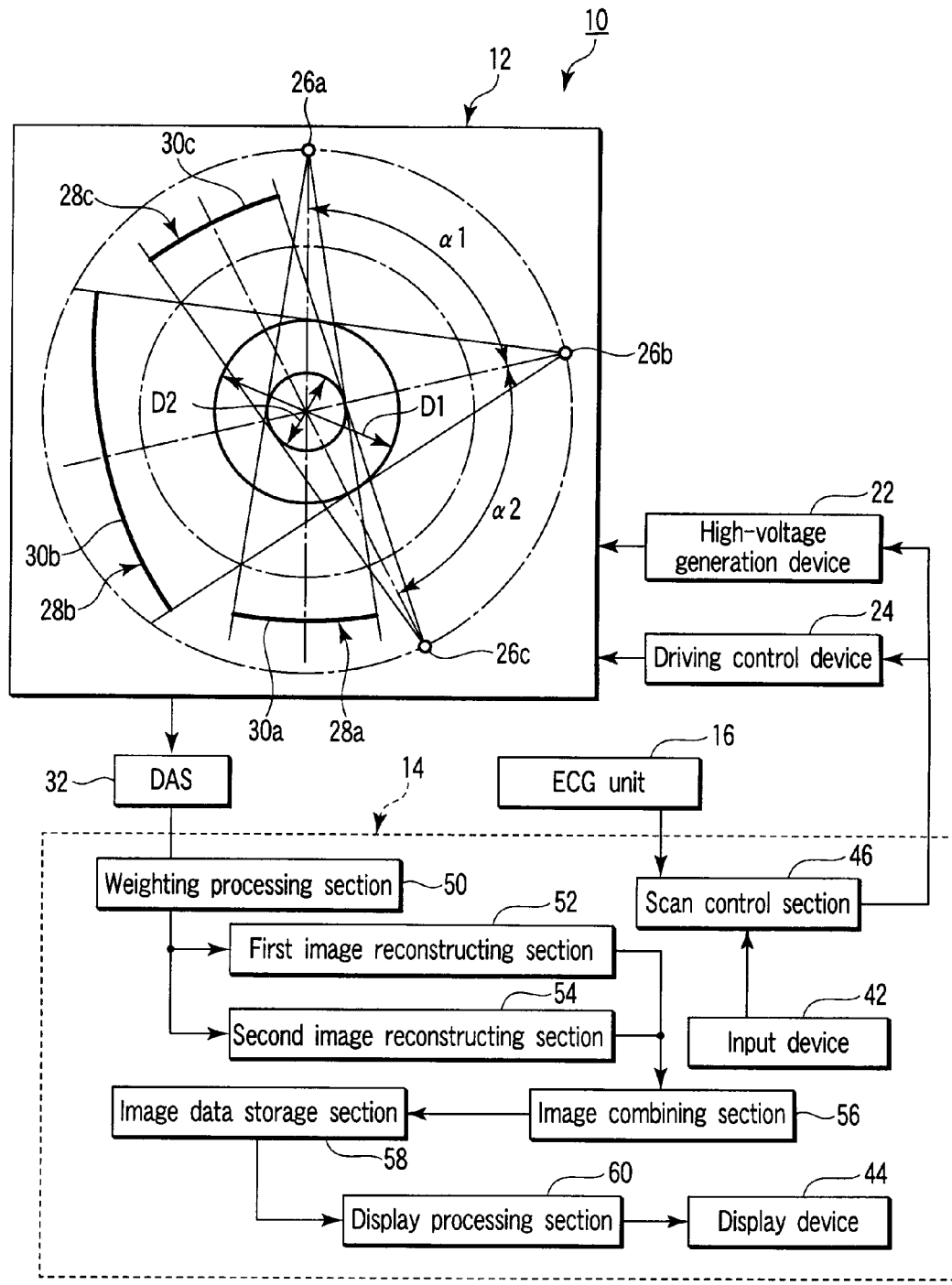
FIG. 5 is a function block diagram showing a first embodiment of an X-ray CT scanner according to the present invention.

FIG. 5 is a function block diagram showing a first embodiment of an X-ray CT scanner according to the present invention.

In FIG. 5, an X-ray CT scanner 10 includes a gantry section 12, a computer device 14, and an ECG unit 16.

The gantry section 12 includes a high-voltage generation device 22, a driving control device 24, a plurality of X-ray tubes, e.g., three X-ray tubes 26a, 26b, and 26c, X-ray detectors 30a, 30b, and 30c which are arranged to face the respective X-ray tubes 26a, 26b, and 26c to form pairs 28a, 28b, and 28c, and a data acquisition system (DAS) 32.

The respective X-ray tubes 26a, 26b, and 26c and the X-ray detectors 30a, 30b, and 30c are arranged on a non-illustrated common rotator. Further, when this rotator is rotated, the respective X-ray tubes 26a, 26b, and 26c and the respective X-ray detectors 30a, 30b, and 30c are rotated on the same plain. This rotator is rotatably supported on a mount fixing portion through a bearing.

The high-voltage generation device 22 provided in the gantry region 12 has a function of irradiating a subject with X-rays from focusing portions (X-ray generating portions) of the respective X-ray tubes 26a, 26b, and 26c by applying a high-voltage to the respective X-ray tubes 26a, 26b, and 26c. Moreover, the driving control device 24 has a function of rotating the X-ray detectors 30a, 30b, and 30c arranged to face the respective X-ray tubes 26a, 26b, and 26c together with these tubes by rotating the rotator.

That is, in the X-ray CT scanner 10, the driving control device 24 rotates the pairs 28a, 28b, and 28c constituted of the X-ray tubes 26a, 26b, and 26c and the X-ray detectors 30a, 30b, and 30c. Additionally, when a high-voltage is applied from the high-voltage generation device 22, the X-ray applied to the non-illustrated subject from each of the X-ray tubes 26a, 26b, and 26c is detected by each of the X-ray detectors 30a, 30b, and 30c arranged to face the respective X-ray tubes 26a, 26b, and 26c. Further, X-ray detection data detected by the X-ray detectors 30a, 30b, and 30c is supplied to a data acquisition system 32 where data is converted into digitized raw data.

Furthermore, the respective pairs 28a, 28b, and 28c constituted of the respective X-ray tubes 26a, 26b, and 26c and the X-ray detectors 30a, 30b, and 30c are desirably arranged at positions where data collection based on half reconstruction can be appropriately carried out. That is, the respective pairs 28a, 28b, and 28c are arranged at positions where angles formed by irradiation directions of X-rays between the pairs 28a, 28b, and 28c adjacent to each other are not uniform in such a manner that a range required for half reconstruction can be covered. Ideally, the respective pairs 28a, 28b, and 28c are arranged at positions obtained by uniformly dividing an angle in the range required for data collection based on half reconstruction. That is, it is desirable to arrange respective bulbs 26a, 26b, and 26c at positions obtained by uniformly dividing an angle appropriate for half reconstruction and arrange the corresponding X-ray detectors 30a, 30b, and 30c at positions facing the respective bulbs 26a, 26b, and 26c.

For example, as shown in FIG. 5, when the range appropriate for data collection based on half reconstruction is 240 degrees and the number of the bulbs 26 is three, the two pairs 28a and 28c are provided at positions on both sides crossing the single pair 28b as a reference at $\alpha 1=\alpha 2=80$ degrees corresponding to ⅓ of the angle 240. It should be noted that the arbitrary pair 28a, 28b, or 28c can be determined as a reference pair, and the reference pair does not have to be the central pair 28b. Furthermore, the angles $\alpha 1$ and $\alpha 2$ depicted in FIG. 5 may be different angles.

However, the respective pairs 28a, 28b, and 28c may be evenly arranged on the rotation plane. This can be likewise applied to an example where the two, four or more pairs 28 are provided.

It should be noted that data in a range that is wide by an amount corresponding to a fan beam angle of the X-ray can be actually collected, but the explanation will be given considering a positional relationship between central lines of the respective pairs 28a, 28b, and 28c alone for simplification.

Moreover, each of the X-ray detectors 30a, 30b, and 30c is a two-dimensional detector, and detection elements for a plurality of channels are arranged in a plurality of columns along a body axis direction (a depth direction in FIG. 5). However, detection elements corresponding to the number of the channels sufficient to cover a wide FOV required for imaging are provided in the X-ray detector 30 constituting at least one pair 28. Additionally, a fan angle of the X-ray tube 26 facing the X-ray detector 30 covering the wide FOV is also set to cover the wide FOV.

On the other hand, detection elements corresponding to the number of the channels sufficient to cover a local FOV (an range smaller than the wide FOV) required for imaging with an improved time resolution are provided in the X-ray detector 30 constituting the other pair 28. Further, a fan angle of the X-ray tube 26 facing the X-ray detector 30 covering the local FOV is also set to cover the local FOV.

For example, the wide FOV is determined to enable imaging the entire subject, and the local FOV is determined to cover a range sufficient for imaging the heart. That is, as shown in FIG. 5, the detection elements corresponding to the number of channels that is approximately 1000 ch sufficient to cover the wide FOV having D1=approximately $\phi 500$ mm are provided in the X-ray detector 30b constituting the central pair 28b. Likewise, the detection elements corresponding to the number of the channels that is approximately 500 ch sufficient to cover the local FOV having D2=approximately $\phi 200$ mm are provided in each of the X-ray detectors 30a and 30c constituting the pairs 28a and 28c on both sides.

On the other hand, the fan angles of the respective X-ray tubes 26a, 26b, and 26c are also set in accordance with the wide FOV and the local FOV. That is, the fan angle of the central X-ray tube 26b is an angle that can cover the wide FOV, and the fan angles of the X-ray tubes 26a and 26c on both sides are angles that can cover the local FOV.

On the other hand, the computer device 14 includes an input device 42, a display device 44, a scan control section 46, a weighting processing section 50, a first image reconstructing section 52, a second image reconstructing section 54, an image combining section 56, an image data storage section 58, and a display processing section 60. All or some of the respective constituent elements can be configured by reading a program into a circuit or a non-illustrated arithmetic operation device.

The ECG unit 16 has a function of acquiring an ECG signal of the non-illustrated subject and supplying this signal to the scan control section 46.

Further, the scan control section 46 has a function of controlling selection or irradiation timings of the bulbs 26a, 26b, and 26c that apply X-rays and rotating angles of the bulbs 26a, 26b, and 26c and the X-ray detectors 30a, 30b, and 30c by supplying a control signal to the high-voltage generation device 22 or the driving control device 24. In particular, the scan control section 46 has a function of acquiring a trigger from the ECG signal received from the ECG unit 16 and outputting a control signal to the high-voltage generation device 22 to execute scanning based on electrocardiographic synchronization.

Furthermore, these functions of the scan control section 46 enable collecting data for image generation by using a desired X-ray detector 30 in the plurality of X-ray detectors 30a, 30b, and 30c. The X-ray detectors 30a, 30b, and 30c used for data collection can be modally switched in accordance with instruction information from the input device 42. For example, a single mode and a dual mode can be set.

Data collection in the single mode corresponds to a mode where the central X-ray tube 26b and the X-ray detector 30b alone are used to collect data for an image. Data collection in the dual mode corresponds to a mode where the central X-ray tube 26b and the X-ray detector 30b are used to collect data with respect to the wide FOV and the respective X-ray tubes 26a, 26b, and 26c and the respective X-ray detectors 30a, 30b, and 30c are used to collect necessary projection data with respect to the local FOV, thereby generating an image with a high time resolution.

In the single mode, since the single X-ray detector 30b is used to collect data, a smooth image without steps can be obtained with respect to the wide FOV. Moreover, in the dual mode, since the plurality of X-ray detectors 30a, 30b, and 30c are used to collect data, an image with a higher time resolution than that in the single mode can be generated with respect to the local FOV. Therefore, an image with less influence of a movement can be obtained from a moving region, e.g., the heart.

The weighting processing section 50 has a function of acquiring raw data obtained by scanning from the data acquisition system 32 and weighting the collected raw data with a weight associated with each of the X-ray detectors 30a, 30b, and 30c. The weight is determined in such a manner that image data combined by a later-explained image combining section 56 becomes smooth in a direction corresponding to a channel direction of the detection element included in each of the X-ray detectors 30a, 30b, and 30c.

The weighting processing section 50 is configured to supply weighted data collected by using the X-ray tubes 26a and 26c and the X-ray detectors 30a and 30c on both sides to the first image reconstructing section 52, and supply weighted data collected by using the X-ray tube 26b and the X-ray detector 30b at the center to the second image reconstructing section 54.

It should be noted that the data collected by using the plurality of X-ray detectors 30a, 30b, and 30c is segmented in accordance with the X-ray detectors 30a, 30b, and 30c, and supplied from the weighting processing section 50 to the first image reconstructing section 52 and the second image reconstructing section 54 in this state. Furthermore, data collected for half reconstruction is data of an angle that is less than 360 degrees, and data collected for usual reconstruction rather than half reconstruction is data in a 360-degree direction.

The first image reconstructing section 52 has a function of performing image reconstruction processing with respect to the weighted data collected by using the X-ray tubes 26a and 26c and the X-ray detectors 30a and 30c on both sides to generate intermediate image data in the local FOV, and a function of supplying the generated intermediate image data in the local FOV to the image combining section 56.

The second image reconstructing section 54 has a function of performing image reconstruction processing with respect to the weighted data collected by using the X-ray tube 26b and the X-ray detector 30b at the center to generate intermediate image data, and a function of supplying the intermediate image data to the image combining section 56.

Moreover, the image combining section 56 has a function of adding and combining the intermediate image data obtained by using the X-ray tubes 26a and 26c and the X-ray detectors 30a and 30c on both sides to the intermediate image data obtained by using the X-ray tube 26b and the X-ray detector 30b at the center to generate image data to be displayed, and a function of writing and saving the generated image data in the image data storage section 58.

The image data storage section 58 has a function of saving the image data generated by the image combining section 56.

The display processing section 60 has a function of reading necessary image data from the image data storage section 58 and displaying the read image data in accordance with instruction information of an image display method received from the input device 42, and a function of supplying the displayed image data to the display device 44 to be displayed. As the display method, there is a display method of displaying the image data generated by the image combining section 56 as it is. As the image data generated by the image combining section 56, there are image data obtained by combining data from the plurality of X-ray detectors 30a, 30b, and 30c in the dual mode, image data obtained by reconstructing data from the single X-ray detector 30b in the single mode.

As examples of other display methods, there are a display method of displaying a boundary between the local FOV and the wide FOV when image data is reconstructed in the dual mode, a display method of displaying image data in the local FOV alone in an enlarging manner in accordance with a size of image data in the wide FOV, a display method of switching and displaying image data in the wide FOV reconstructed in the single mode and image data in the wide FOV reconstructed in the dual mode, a display method of switching and displaying image data in the local FOV reconstructed in the single mode and image data in the local FOV reconstructed in the dual mode, a display method of displaying whether data is image data reconstructed in the single mode or image data reconstructed in the dual mode, and others.

Operations and functions of the X-ray CT scanner 10 will now be explained.

It should be noted that, as shown in FIG. 5, a description will be given on an example where the X-ray CT scanner 10 in which the pairs 28a and 28c covering the two local FOVs are arranged at positions crossing the pair 28b covering the central wide FOV on both sides at 80 degrees is used to execute electrocardiographic synchronized imaging with respect to the wide FOV including the heart.

First, it is assumed that the input device 42 supplies an instruction of imaging the subject in, e.g., the dual mode to the scan control section 46. Then, in synchronization with an ECG signal from the ECG unit 16, the scan control section 46 supplies control signals to the high-voltage generation device 22 and the driving control device 24.

Moreover, the driving control device 24 rotates the pairs 28a, 28b, and 28c of the X-ray tubes 26a, 26b, and 26c and the X-ray detectors 30a, 30b, and 30c. At this time, the pairs 28a, 28b, and 28c of the X-ray tubes 26a, 26b, and 26c and the X-ray detectors 30a, 30b, and 30c are rotated at an angle enabling the X-ray detector 30b at the center to collect data required for at least half reconstruction from the wide FOV.

Additionally, during rotation of the X-ray tubes 26a, 26b, and 26c and the X-ray detectors 30a, 30b, and 30c, the high-voltage generation device 22 applies a high voltage to each of the X-ray tubes 30a, 30b, and 30c, thereby irradiating the non-illustrated subject with X-rays. Further, the X-rays transmitted through the subject are detected by the X-ray detectors 30a, 30b, and 30c arranged to face the respective X-ray tubes 26a, 26b, and 26c. However, the X-ray tube 26b at the center emits the X-ray in such a manner that the X-ray detector 30b can detect data required for half reconstruction from the wide FOV.

On the other hand, the respective X-ray tubes 26a and 26c on both sides emit the X-rays in such a manner that the data from the local FOVS can be segmented and detected by the respective X-ray detectors 30a, 30b, and 30c.

For example, when a data collection range for half reconstruction is 240 degrees, the X-ray tubes 26a, 26b, and 26c and the X-ray detectors 30a, 30b, and 30c are rotated 240 degrees. Furthermore, the X-ray detector 30b at the center detects data corresponding to 240 degrees. On the other hand, the two X-ray detectors 30a and 30c on both sides detect data corresponding to 80 degrees.

FIG. 6 is a conceptual view for explaining a method of using the X-ray CT scanner 10 depicted in FIG. 5 to detect data for half reconstruction by the three X-ray detectors 30a, 30b, and 30c in synchronization with the ECG signal. FIG. 7 is another conceptual view for explaining a method of using the X-ray CT scanner 10 depicted in FIG. 5 to detect data for half reconstruction by the three X-ray detectors 30a, 30b, and 30c in synchronization with the ECG signal.

As shown in FIG. 6, the three X-ray detectors 30a (SUB 1), 30b (MAIN), and 30c (SUB 2) detect data for half reconstruction in a beat period tb of the ECG signal. That is, the X-ray emitted in a range R240 of 240 degrees in the wide range FOV (a diameter D1) from the bulb 26b at the center is detected by the corresponding X-ray detector 30b (MAIN). Moreover, the X-rays emitted in a range R80 of 80 degrees in the local FOV (a diameter D2) from the respective X-ray tubes 26a and 26c on both sides are detected by the X-ray detectors 30a (SUB 1) and 30c (SUB 2). Here, in view of improving a time resolution of the X-ray CT scanner 10, the X-ray detectors 30a (SUB 1) and 30c (SUB 2) on both sides and the X-ray detector 30b (MAIN) at the center simultaneously detect data corresponding to 80 degrees in each local FOV.

Here, when the number of beats per minute is 120, a time tb of one heartbeat is 0.5 s. On the other hand, when a rotating speed of each of the bulbs 26a, 26b, and 26c is 0.3 s/rotation, a time required for 80-degree rotation is 80/360×0.3≅0.07 s. That is, when the X-ray detectors 30a (SUB 1) and 30c (SUB 2) on both sides and the X-ray detector 30b (MAIN) at the center simultaneously detect data, a time required to collect data corresponding to 240 degrees in the local FOV is 0.07 s, thereby realizing an excellent time resolution with respect to the time of one heartbeat.

Therefore, as indicated by a bulb trajectory P in FIG. 7, when helically moving the bulbs 26a, 26b, and 26c around the subject, the three X-ray detectors 30a (SUB 1), 30b (MAIN), and 30c (SUB 2) can simultaneously divide data corresponding to 240 degrees in a reconstruction plane Y in one heartbeat and the divided data can be collected from different regions in relation to the local FOV.

Additionally, the thus detected X-rays are supplied to the data acquisition system 32 to be converted into raw data, and the converted data is output to the computer device 14. The computer device 14 performs image processing of the raw data.

Figure 8:
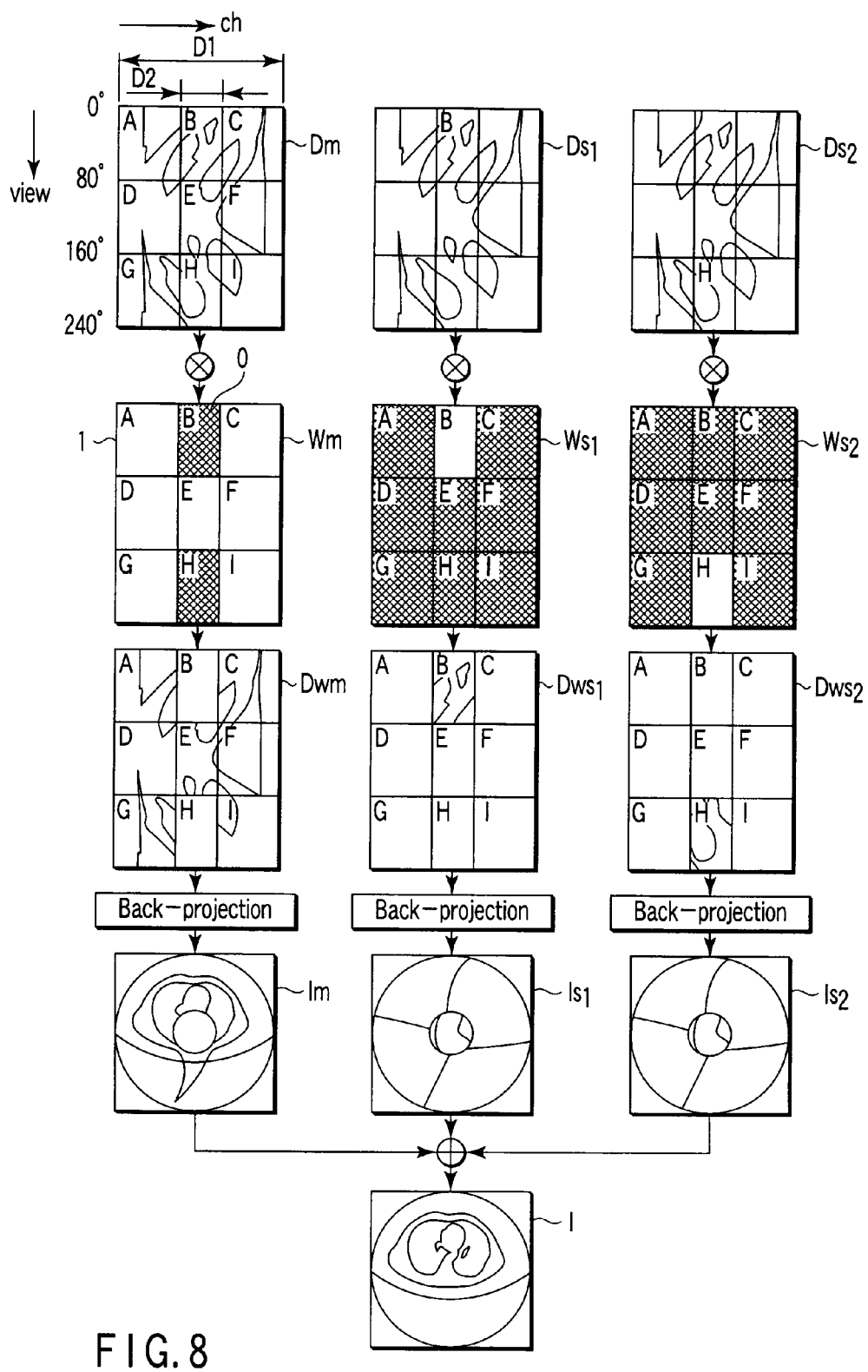
FIG. 8 is a flowchart showing a flow of image processing in a computer device depicted in FIG. 5.

FIG. 8 is a flowchart showing a flow of image processing in the computer device 14 depicted in FIG. 5, and reference numbers with S in the drawing denote respective steps in the flowchart.

In FIG. 8, Dm, Ds1, and Ds2 in the drawing denote sinogram regions detected by the X-ray detector 30b (MAIN) at the center and the X-ray detectors 30a (SUB 1) and 30c (SUB 2) on both sides, respectively. That is, the sinogram can be divided into nine regions represented as A to I by three-way division along a channel direction and a view direction (a projection direction).

Since the X-ray detector 30b (MAIN) at the center detects data in a channel covering the wide FOV, it can collect data from all regions in the channel direction. Further, the X-ray detector 30b (MAIN) at the center collects data in a 240-degree direction required for half reconstruction, data in the view direction can be collected from all regions. Therefore, the sinogram region Dm detected by the X-ray detector 30b (MAIN) at the center is constituted of the nine regions A to I.

Since the X-ray detector 30a (SUB 1) on one side detects data in a channel covering the local FOV alone, data from the central region alone corresponding to the local FOV in the channel direction can be collected. Furthermore, of the data in the 240-degree direction required for half reconstruction, data corresponding to, e.g., first 80 degrees is collected by the X-ray detector 30a (SUB 1) on one side, thereby collecting data from a region corresponding to the first 80-degree direction alone in regard to the view direction. Therefore, the sinogram region Ds1 detected by the X-ray detector 30a (SUB 1) alone is region B alone.

Since the X-ray detector 30c (SUB 2) on the other side detects data in a channel covering the local FOV alone, data can be collected from a central region alone corresponding to the local FOV in the channel direction. Moreover, of the data in the 240-degree direction required for half reconstruction, data corresponding to, e.g., last 80 degrees is collected by the X-ray detector 30c (SUB 2) on the other side, thereby collecting data from a region corresponding to the last 80-degree direction alone. Therefore, the sinogram region Ds2 detected by the X-ray detector 30c (SUB 2) on the other side is region H alone.

Moreover, the respective sinograms detected by the X-ray detector 30b (MAIN) at the center and the X-ray detectors 30a (SUB 1) and 30c (SUB 2) on the sides are supplied to the weighting processing section 50 from the data acquisition system 32.

The weighting processing section 50 generates weighting window functions associated with the X-ray detectors 30a, 30b, and 30c that have collected the respective sinograms. Each window function may be previously produced before imaging. The respective window functions are generated for weighting processing for data collected by the X-ray detectors 30a, 30b, and 30c. Therefore, each window function is generated in such a manner that a weight varies depending on a position in the channel direction and the view direction. In more detail, each window function is generated in such a manner that the weight becomes "1" in a region of data used for image generation and the weight becomes "0" in a region of data that is not used for image generation.

Of the data collected by the central X-ray detector 30b (MAIN), it is desirable for a region of data used for image generation to be a region from which data cannot be simultaneously detected by the X-ray detectors 30a (SUB 1) and 30c (SUB 2) on the sides. That is because simultaneously collecting data from a region from which data can be collected by the X-ray detectors 30a (SUB 1) and 30c (SUB 2) on the sides, i.e., the local FOV by the central X-ray detector 30b (MAIN) and the X-ray detectors 30a (SUB 1) and 30c (SUB 2) on the sides in accordance with each segment is important for acquisition of a high time resolution.

Then, in regard to the window function Wm for the data collected by the central X-ray detector 30b (MAIN), the weight becomes "0" in region B from which data can be simultaneously collected by the X-ray detector 30a (SUB 1) on one side in accordance with each segment and region H from which data can be simultaneously collected by the X-ray detector 30c (SUB 2) on the other side in accordance with each segment. Conversely, the weight of the window function Wm becomes "1" in other regions A, C, D, E, F, G, and I.

Additionally, a weight of the window function Wsl for the data collected by the X-ray detector 30a (SUB 1) on one side becomes "1" in region B from which data can be simultaneously collected by the X-ray detector 30a (SUB 1) in accordance with each segment. Conversely, the weight of the window function Ws1 becomes "0" in other regions A, C, D, E, F, G, and I. Likewise, a weight of the window function Ws2 for the data collected by the X-ray detector 30c (SUB 2) on the other side becomes "1" in region H from which data can be simultaneously collected by the X-ray detector 30c (SUB 2) in accordance with each segment. Conversely, the weight of the window function Ws2 becomes "0" in other regions A, B, C, D, E, F, G, and I.

However, the weights of the respective window functions Wm, Ws1, and Ws2 are determined in such a manner that an image value smoothly varies at a boundary part in the channel direction when the respective pieces of data weighted based on the respective window functions Wm, Ws1, and Ws2 are combined to general a single piece of image data. That is, the weights of the respective window functions Wm, Ws1, and Ws2 are determined in such a manner that weighting percentages of respective pieces of projection data corresponding to different detectors gradually vary from one to the other at a boundary part between these pieces of data in the channel direction in the combined image data.

Figures 9A, 9B:
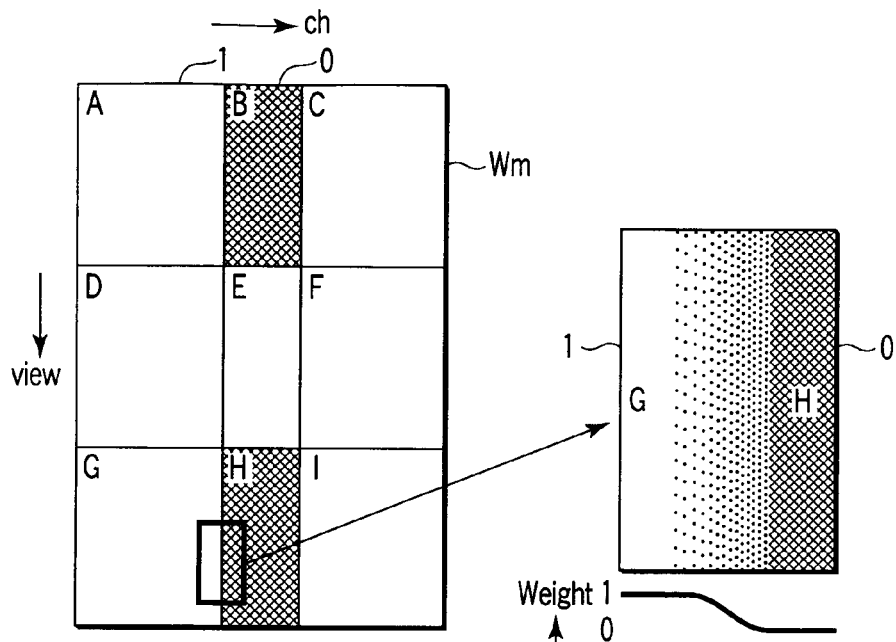
FIG. 9A is an enlarged view of a window function Wm with respect to data collected by a central X-ray detector (MAIN) depicted in FIG. 8.
FIG. 9B is a view for explaining a weight of a boundary part in a channel direction in FIG. 9A.

FIG. 9A is an enlarged view of the window function Wm for the data collected by the central X-ray detector 30b (MAIN) depicted in FIG. 8.

As shown in FIG. 9A, the weight of the window function Wm for the data collected by the central X-ray detector 30b (MAIN) is "0" in region B and region H. On the other hand, the weight becomes "1" in other regions A, C, D, E, F, G, and I. Moreover, the respective pieces of data in region B, region E, and region H are simultaneously collected by the X-ray detectors 30b (MAIN), 30a (SUB 1), and 30c (SUB 2) in accordance with each segment, and the collected pieces of data are combined with each other. However, when the window function Wm digitally varies from "0" to "1", a step may be produced at the boundary part of the combined image data.

Thus, as shown in FIG. 9B, the weight of the window function Wm is determined in such a manner that the weight at the boundary part between regions B, and H where the weight is "0" and regions A, C, D, E, F, G, and I where the weight is "1" in the channel direction smoothly varies from "1" to "0" or from "0" to "1". When the data is subjected to weighting and addition by using the window function having the weight that smoothly varies, the boundary part between the respective pieces of data in the channel direction can be gradually changed from one to the other.

It should be noted that the weighting processing may be carried out with respect to not only the channel direction but also the view direction in such a manner that the weighting percentages of both pieces of projection data corresponding to different detectors gradually vary from one to the other.

When the respective pieces of data collected by the corresponding X-ray detectors 30a, 30b, and 30c are multiplied by the respective window functions Wm, Ws1, and W2 determined in this manner, the data can be weighted. That is, the respective X-ray detectors 30a, 30b, and 30c can cut out data used for image data generation from the respective pieces of collected data.

That is, as shown in FIG. 8, multiplying the data in the region Dm collected by the central X-ray detector 30b (MAIN) by the window function Wm enables generating data Dwm from which the data in region B and region H detected by the X-ray detectors 30a (SUB 1) and 30c (SUB 2) on the sides is removed. Further, multiplying the data in the region Ds1 collected by the X-ray detector 30a (SUB 1) on one side by the window function Ws1 enables generating data Dws1 in the region Ds1 collected by the X-ray detector 30a (SUB 1). Likewise, multiplying the data in the region Ds2 collected by the X-ray detector 30c (SUB 2) on the other side by the window function Ws2 enables producing data Dws2 in the region Ds2 collected by the X-ray detector 30c (SUB 2).

The weighting processing section 50 weights each data collected by each X-ray detector 30b (MAIN), 30a (SUB 1), or 30c (SUB 2) in this manner. Furthermore, the weighting processing section 50 supplies the weighted data Dws1 and Dws2 collected by using the X-ray detectors 30a (SUB 1) and 30c (SUB 2) on the sides to the first image reconstructing section 52. Moreover, the weighting processing section 50 supplies the weighted data Dwm collected by using the central X-ray detector 30b (MAIN) to the second image reconstructing section 54.

Then, the first image reconstructing section 52 performs image reconstruction processing involving back-projection processing with respect to the respective pieces of weighted data Dws1 and Dws2 collected by using the X-ray detectors 30a (SUB 1) and 30c (SUB 2) on the sides, thereby generating SUB images Is1 and Is2 as intermediate image data in the local FOV. Additionally, the first image reconstructing section 52 supplies the generated SUB images Is1 and Is2 to the image combining section 56.

On the other hand, the second image reconstructing section 54 performs image reconstruction processing involving back-projection processing with respect to the weighted data Dwm collected by using the central X-ray detector 30b (MAIN), thereby producing a main image Im as intermediate image data. Additionally, the second image reconstructing section 54 supplies the generated main image Im to the image combining section 56.

Then, the image combining section 56 adds and combines the SUB images Is1 and Is2 received from the first image reconstructing section 52 to the main image Im received from the second image reconstructing section 54 to generate image data I to be displayed. Further, the image combining section 56 writes the generated image data I for display in the image data storage section 58. As a result, the image data generated by the image combining section 56 is stored in the image data storage section 58.

As a result, when information indicating an image display method and an instruction of displaying the image data I are supplied from the input device 42 to the display processing section 60, the image data I can be displayed in the display device 44 by the indicated image display method.

Figure 10:
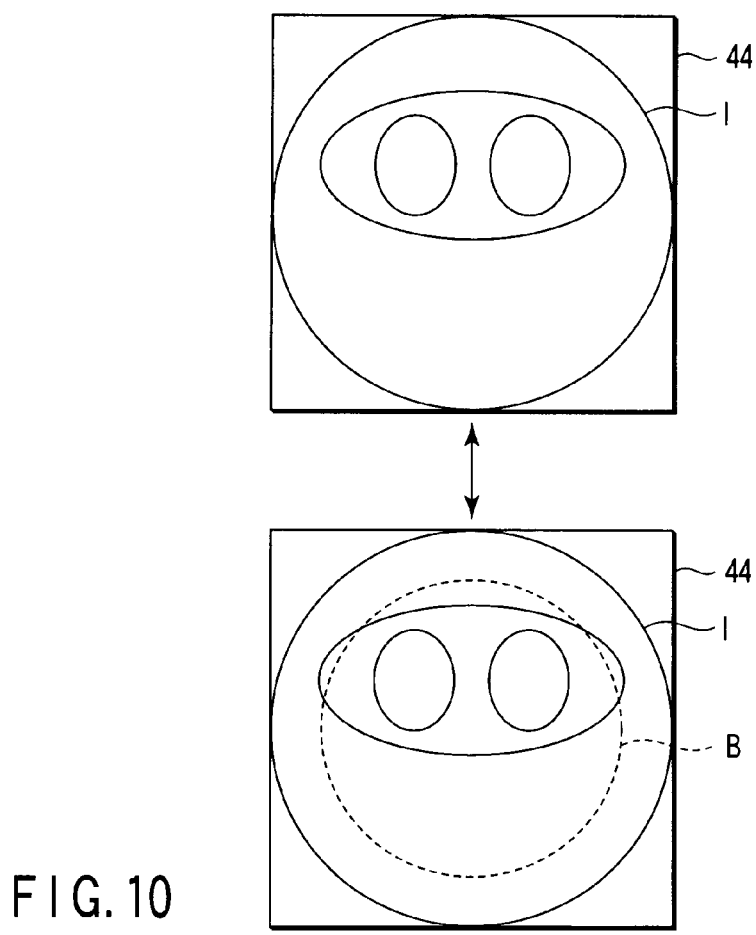
FIG. 10 is a view showing an example where a boundary between a local FOV and a wide FOV is shown in image data I displayed in a display device depicted in FIG. 5.

FIG. 10 is a view showing an example where a boundary between the local FOV and the wide FOV is shown in the image data I displayed in the display device 44 depicted in FIG. 5.

When an instruction is supplied to the display processing section 60 from the input device 44, display/non-display of a boundary B between the local FOV and the wide FOV on the image data can be switched as shown in FIG. 10. In this case, an upper side of FIG. 10 shows a non-display state, and a lower side of FIG. 10 shows a display state. When multi-bulb imaging is carried out, characteristics, e.g., an image reconstruction technique in and out of the local FOV, a resolution, a spatial resolution, noise, a time resolution, and others may vary in some cases. Therefore, discontinuity or an artifact of an image may occur at the boundary B between the local FOV and the wide FOV.

Thus, the boundary B between the local FOV and the wide FOV can be displayed in the form of a line so that a user can recognize a difference in characteristics between respective regions. Furthermore, adjusting a line width of the line indicative of the boundary B enables hiding a step or an artifact on the boundary B.

If an icon for switching, e.g., a non-illustrated button is displayed in the display device 44 and display/non-display of the boundary B between the local FOV and the wide FOV can be switched through a single-touch operation of the input device 42, convenience for users can be improved.

Moreover, sizes of the local FOV and the wide FOV can be changed by moving the boundary line to vary a size of a circle. In this case, when a position of the boundary between regions B, E, and H and regions A, D, and G (or regions C, F, and I) in the channel direction is changed in accordance with a size of the circle of this boundary line to perform reconstruction processing, images of a region of a low time resolution in a wide range (a region of the wide FOV) and a high time resolution in a narrow range (a region of the local FOV) corresponding to the boundary line can be obtained.

FIG. 11 is a view showing an example where the image data I1 in the local FOV alone is displayed in the display device 44 depicted in FIG. 5 in an enlarging manner in accordance with a size of the image data I in the wide FOV. In this case, an upper side of FIG. 11 shows a display state and a lower side of FIG. 11 shows an enlarged display state.

As shown in FIG. 11, the image data I1 in the local FOV alone can be displayed in an enlarging manner in accordance with a size of the image data I in the wide FOV. If enlarged display of this image data can be switched through a single-touch operation of the input device 42, convenience for users can be improved.

FIG. 12 is a view showing an example where image data in the wide FOV reconstructed in the single mode and image data in the wide FOV reconstructed in the dual mode are switched and displayed in the display device 44 depicted in FIG. 5. In this case, an upper side of FIG. 12 shows a display state in the dual mode, and a lower side of FIG. 12 shows a display state in the single mode.

Although multi-bulb imaging in the dual mode has been explained in the example depicted in FIG. 8, data detected by the central X-ray detector 30b (MAIN) alone that covers the wide FOV can be used to generate image data to be displayed. When an image is reconstructed from the data collected by using the central X-ray detector 30b (MAIN) alone, a time resolution is not improved, but an image without a step or artifact at the boundary between the local FOV and the wide FOV can be obtained.

Incidentally, if the image data for display is reconstructed by using the data detected by the central X-ray detector 30b (MAIN) that covers the wide FOV of the data collected by the respective X-ray detectors 30b (MAIN), 30a (SUB 1), and 30c (SUB 2), image data equivalent to the image data generated from the data collected in the single mode can be obtained. Therefore, in this case, data collection is carried out in the dual mode, but image reconstruction is performed in the single mode.

Thus, as shown in FIG. 12, image data Is in the wide FOV reconstructed in the single mode and image data Id in the wide FOV reconstructed in the dual mode can be switched and displayed. This switching display can be performed through a single-touch operation of the input device 42. Moreover, as shown in FIG. 12, information indicating whether image data is reconstructed in the single mode or reconstructed in the dual mode can be displayed.

FIG. 13 is a view showing an example where image data in the local FOV reconstructed in the single mode and image data in the local FOV reconstructed in the dual mode are switched and displayed in the display device 44 depicted in FIG. 5.

Like the image data Is and Id in the wide FOV, in regard to the image data I1 in the local FOV, image data I1d reconstructed in the dual mode and image data I1s reconstructed in the single mode can be switched and displayed as shown in FIG. 13. This switching display can be performed through a single-touch operation of the input device 42.

Additionally, as shown in FIG. 13, information indicating whether image data is reconstructed in the single mode or reconstructed in the dual mode can be displayed.

Switching the display method in this manner enables a user to assuredly recognize a boundary at which characteristics of an image quality vary or a reconstruction mode in image data. Therefore, reading errors can be reduced.

That is, according to the above-explained X-ray CT scanner 10, in the multi-bulb CT including the plurality of bulbs, when fan angles of the systems each constituted of each bulb and a corresponding X-ray detector differ from each other, combining a plurality of pieces of data collected by the respective systems based on electrocardiographic synchronization enables locally reconstructing an image with a high time resolution.

That is, in the multi-bulb CT, the FOV that is covered by all the bulbs is an FOV from each data can be collected by a bulb having the smallest fan angle and a corresponding X-ray detector. In other words, the FOV that is covered by all the bulbs is determined based on the minimum bulb fan angle.

For example, in case of the X-ray CT scanner 10 depicted in FIG. 5, the three bulbs 26a, 26b, and 26c cover the FOV having the diameter D2. Therefore, when image data is just generated from data collected by the plurality of bulbs based on the regular image reconstruction technique, the image data cannot be reconstructed even if data is collected from a region outside the FOV covered by all the bulbs.

Thus, according to the X-ray CT scanner 10, a plurality of pieces of intermediate image data reconstructed by weighting raw data collected by using the plurality of X-ray detectors 30 are combined, thereby reconstructing image data in the wider FOV. For example, in regard to the local FOV, image data is reconstructed from data simultaneously collected by using the plurality of X-ray detectors 30 in accordance with each segment. In regard to the region outside the local FOV, data collected by the X-ray detector that covers the outside of the local FOV can be used to generate image data based on half reconstruction.

Therefore, according to the X-ray CT scanner 10, imaging with a high time resolution can be performed by irradiating the local FOV alone with X-rays from a plurality of directions without irradiating the entire wide FOV that can be imaged with X-rays from the plurality of directions. In order words, the local FOV alone requiring a high time resolution can be irradiated with X-rays from the plurality of directions. Therefore, an increase in an exposure amount of the subject in the multi-bulb CT can be suppressed. Furthermore, sizes of some of the X-ray detectors can be reduced. As a result, a distance between the X-ray detectors can be decreased, and a better time resolution can be assured.

Moreover, when weighting is performed in such a manner that a boundary part of image data generated by combining a plurality of pieces of intermediate image data in the channel direction becomes smoothly continuous, artifacts in the image data can be reduced, thereby providing an excellent X-ray CT image.

Additionally, displaying information indicating that image data is reconstructed in the dual mode where data from the plurality of X-ray detectors 30 is used to perform reconstruction and the single mode where data from the single X-ray detector 30 is used to perform reconstruction enables reducing occurrence of reading errors in the image data obtained based on the multi-bulb CT.

Second Embodiment

The X-ray CT scanner including the plurality of (three) imaging systems each having the X-ray tube and the X-ray detector forming a pair with the X-ray tube has been explained in the first embodiment. In this second embodiment, an example where data collected by each asymmetrical detector is utilized to reconstruct an electrocardiographic synchronized image in an X-ray CT scanner including a plurality of imaging systems each having an X-ray tube and an X-ray asymmetrical detector will be explained.

It should be noted that basic structure and operations of the X-ray CT scanner in the second embodiment are the same as those in the first embodiment, and hence like reference numbers denote like parts to omit illustrations and explanations of these parts in order to avoid repeated description, and different parts alone will be explained.

In general, when using collected data obtained from an asymmetrical detector to perform image reconstruction, a data range in an asymmetrical region is filled with opposite data approximately generated from actual data to perform image reconstruction. In the image reconstruction where the data range is filled with opposite data as such approximate data, since an image quality in an asymmetrical region is degraded, data in an asymmetrical region is subjected to image reconstruction by utilizing data from other asymmetrical detector in this second embodiment.

An example of asynchronous reconstruction for conventional scan will be first explained.

Figure 14:
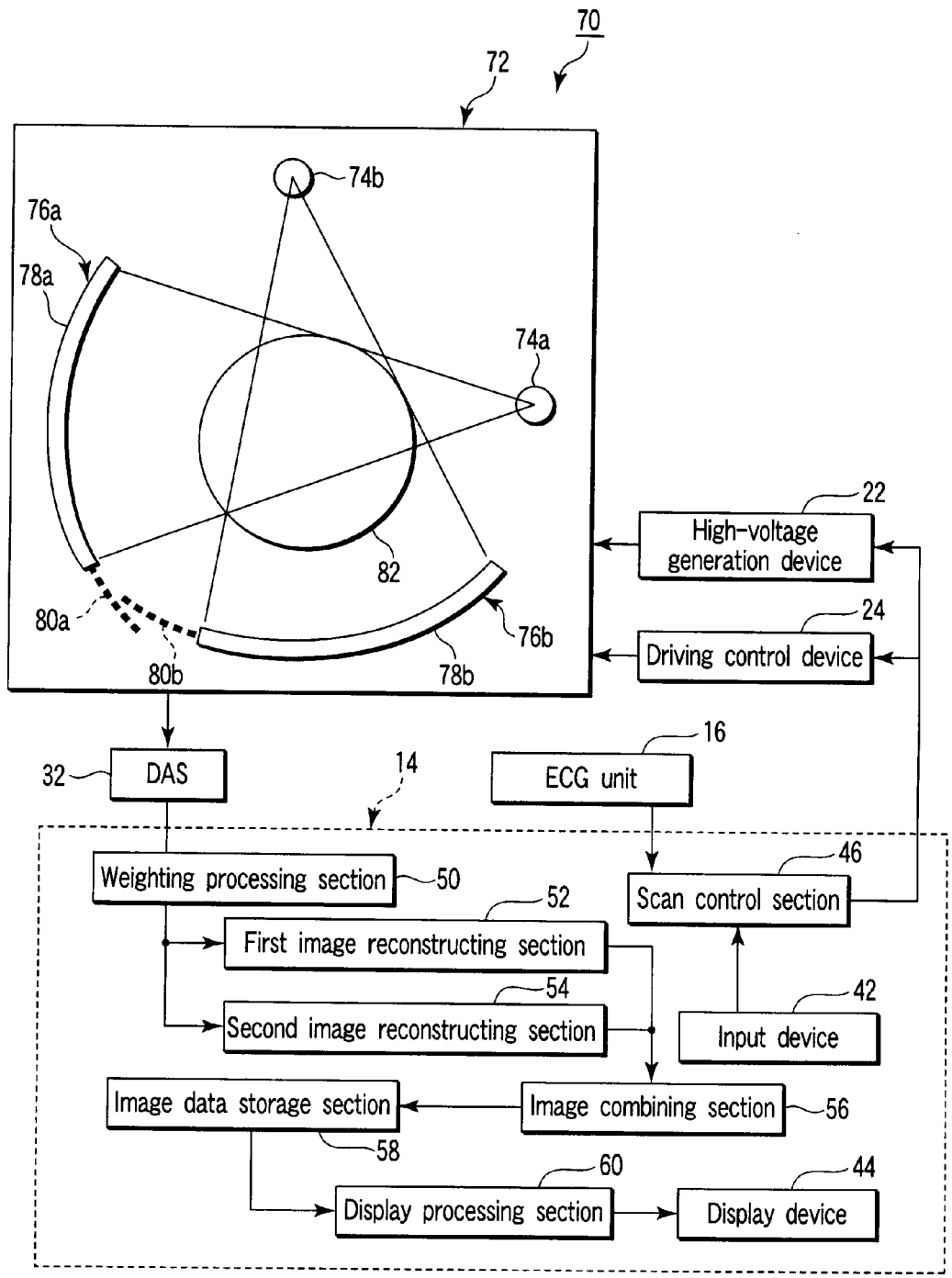
FIG. 14 is a function block diagram showing a second embodiment of an X-ray CT scanner according to the present invention.

FIG. 14 is a function block diagram showing a second embodiment of an X-ray CT scanner according to the present invention.

In FIG. 14, an X-ray CT scanner 70 includes a gantry section 72, a computer device 14, and an ECG unit 16.

The gantry section 72 includes a high-voltage generation device 22, a driving control device 24, a plurality of X-ray tubes, e.g., two X-ray tubes 74a and 74b, X-ray asymmetrical detectors 78a and 78b that are arranged to face the respective X-ray tubes 74a and 74b to form pairs 76a and 76b with these tubes, and a data acquisition system (DAS) 32.

The respective X-ray tubes 74a and 74b and the X-ray asymmetrical detectors 78a and 78b are arranged on a non-illustrated common rotator. Further, when this rotator is rotated, the respective X-ray tubes 74a and 74b and the respective X-ray asymmetrical detectors 78a and 78b are rotated on the same plane. This rotator is rotatably supported on a mount fixing portion through a bearing.

The high-voltage generation device 22 provided in the gantry section 72 has a function of irradiating a subject 82 with X-rays from focusing portions (X-ray generating portions) of the respective X-ray tubes 74a and 74b by applying a high voltage to the respective X-ray tubes 74a and 74b. Furthermore, the driving control device 24 has a function of rotating the X-ray asymmetrical detectors 78a and 78b arranged to face the respective X-ray tubes 74a and 74b together with these tubes by rotating the rotator.

That is, in the X-ray CT scanner 70, the driving control device 24 rotates the pairs 76a and 76b of the X-ray tubes 74a and 74b and the X-ray asymmetrical detectors 78a and 78b. Moreover, when a high voltage is applied from the high-voltage generation device 22, the X-ray asymmetrical detectors 78a and 78b arranged to face the respective X-ray tubes 74a and 74b detect the X-rays applied to the subject 82 from the respective X-ray tubes 74a and 74b. X-ray detection data detected by the X-ray asymmetrical detectors 78a and 78b is supplied to the data acquisition system 32 where the supplied data is converted into digitized raw data.

It should be noted that asymmetrical regions (regions where data is not present) 80a and 80b that cannot be detected by the X-ray asymmetrical detectors 78a and 78b with respect to the X-rays emitted from the respective X-ray tubes 74a and 74b are present in the X-ray asymmetrical detectors 78a and 78b.

Projection data collected by the X-ray asymmetrical detectors 78a and 78b and image reconstruction using the projection data will now be explained with reference to a flowchart of FIG. 15.

Figure 15:
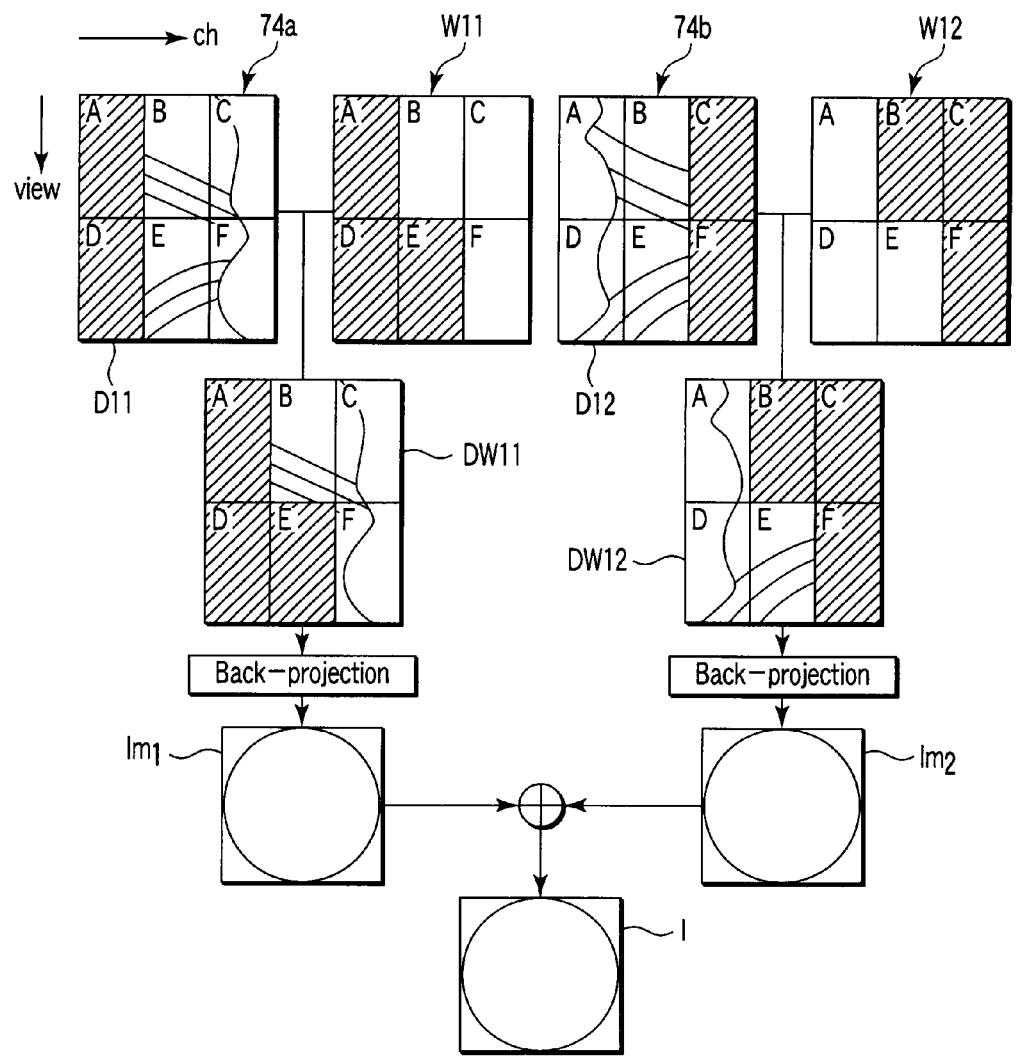
FIG. 15 is a flowchart showing a flow of image processing in a computer device depicted in FIG. 14.

In FIG. 15, D11 and D12 in the drawing denote sinogram regions respectively detected by the X-ray asymmetrical detectors 74a and 74b. That is, the sinogram can be divided into six regions represented as "A to F" by three-way division in a channel direction and two-way division in a view direction (a projection direction).

Of these regions, the sinogram region D11 detected by the X-ray asymmetrical detector 78a is divided into the four regions B, C, E, and F. That is because regions A and D serve as an asymmetrical region 80a. Likewise, the sinogram region D12 detected by the X-ray asymmetrical detector 78b is divided into the four regions A, B, D, and E. That is because regions C and F serve as an asymmetrical region 80b. In this manner, the asymmetrical regions 80a and 80b in the X-ray asymmetrical detector 78a and the X-ray asymmetrical detector 78b have an inverse positional relationship.

Additionally, the respective sinograms detected by the X-ray asymmetrical detector 78a and the X-ray asymmetrical detector 78b are supplied from the data acquisition system 32 to a weighting processing section 50.

The weighting processing section 50 generates window functions having weights respectively associated with the X-ray asymmetrical detectors 78a and 78b that have collected the respective sinograms. The window functions may be previously generated before imaging. The respective window functions are generated to weight data respectively collected by the X-ray asymmetrical detectors 78a and 78b. Therefore, the respective window functions are generated in such a manner that weights vary depending on a position in the channel direction and the view direction. In more detail, each window function is generated in such a manner that the weight becomes "1" in a region of data used for image generation and the weight becomes "0" in a region of data that is not used for image generation.

In regard to a window function W11 for data D11 collected by the X-ray asymmetrical detector 78a, a weight becomes "0" in regions A, D, and E. Conversely, the weight of the window function "11 becomes "1" in the other regions B, C, and F. Likewise, in regard to a window function W12 for data D12 collected by the X-ray asymmetrical detector 78b, a weight becomes "0" in regions B, C, and F and becomes "1" in other regions A, D, and E.

Further, when the respective window functions W11 and W12 determined in this manner are combined with the respective pieces of data D11 and D12 collected by the corresponding X-ray asymmetrical detectors 78a and 78b, the data can be weighted. That is, the respective X-ray asymmetrical detectors 78a and 78b can cut out data used for image data generation from the respective collected pieces of data.

That is, as shown in FIG. 15, when the window function W11 is combined with data in the region D11 collected by the X-ray asymmetrical detector 78a, data Dw11 is generated. Likewise, when the window function W12 is combined with data in the region D12 collected by the X-ray asymmetrical detector 78b, data Dw12 is generated.

The weighting processing section 50 weights the respective pieces of data collected by the X-ray asymmetrical detectors 78a and 78b in this manner. Furthermore, the weighting processing section 50 supplies the pieces of weighted data Dw11 and Dw12 collected by using the X-ray asymmetrical detectors 78a and 78b to a first image reconstructing section 52.

Then, the first image reconstructing section 52 performs image reconstruction processing involving back-projection processing to the respective pieces of weighted data Dw11 and Dw12 collected by using the X-ray asymmetrical detectors 78a and 78b, thereby generating images Im1 and Im2 as intermediate image data. Moreover, the first image reconstructing section 52 supplies the generated images Im1 and Im2 to an image combining section 56.

Subsequently, the image combining section 56 adds and combines the images Im1 and Im2 received from the first image reconstructing section 52, thereby generating image data I to be displayed. Additionally, the image combining section 56 writes the generated image data I for display in an image data storage section 58. As a result, the image data generated by the image generating section 56 is stored in the image data storage section 58.

As explained above, an image quality in an asymmetrical region can be prevented from being degraded by utilizing actual data of the two X-ray asymmetrical detectors rather than filling data that is approximately defective.

An example of synchronous reconstruction for conventional scan will now be explained.

This synchronous reconstruction for conventional scan is carried out by the same method as the asynchronous reconstruction for conventional scan. Weighting is carried out in a fan direction and the view direction by using electrocardiographic data based on various kinds of synchronous reconstruction methods. For example, a light ray that cannot be converged in one system (a system A) can be converged in the other system (a system B), and hence defining a weight in the system B to compensate this state can suffice.

Additionally, although the embodiment about asynchronous/synchronous reconstruction at the time of conventional scan has been explained, since the weights are defined in the fan direction and the view direction, this method can be applied to asynchronous/synchronous reconstruction for helical scan. However, as premises, the reconstruction method is approximate solution cone beam helical reconstruction.

It should be noted that the present invention can be applied to not only a medical X-ray CT scanner but also an industrial X-ray CT scanner that checks devices or an X-ray CT scanner for baggage inspection at, e.g., an airport.

Although the embodiments according to the present invention have been explained above, besides the foregoing embodiments, the present invention can be modified in many ways without departing from the scope of the present invention.

Further, the foregoing embodiments include the invention on various stages, and various inventions can be obtained based on appropriate combinations of a plurality of disclosed structural requirements. For example, if the problems explained in the section "Problems to be Solved by the Invention" can be solved and the effects explained in the section "Effects of the Invention" can be obtained even though some of all structural requirements are deleted, a structure in which these structural requirements are deleted can be obtained as the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT scanner comprising:
    a plurality of X-ray tubes including a first X-ray tube having a first fan angle and a second X-ray tube having a second fan angle larger than the first fan angle;
    a plurality of X-ray detectors which are respectively arranged to face the first X-ray tube and the second X-ray tube and include a first X-ray detector and a second X-ray detector having detection elements;
    a collection data processing section which cuts out and omits from the plurality of pieces of collection data, pieces of (1) data simultaneously collected by the first X-ray detector and the second X-ray detector from a first imaging field of view covered by the first X-ray detector in accordance with each segment and (2) data collected by the second X-ray detector from a region in a second field of view covered by the second X-ray detector outside the first imaging field of view so that the first and second collection data each have respective defective portions corresponding to regions outside the respective imaging fields of view of the first and second X-ray tubes, and smoothly executes weighting processing with respect to remaining pieces of collection data including first collection data obtained by the first X-ray detector and second collection data obtained by the second X-ray detector in a direction corresponding to a channel direction of the detection elements of the plurality of X-ray detectors; and
    a first image generating section which performs image reconstruction processing with respect to the first and second collection data weighted by the collection data processing section to generate complete image data, comprising,
    a first image reconstructing section that performs image reconstruction processing with respect to the first collection data weighted by the collection data processing section to generate first intermediate image data, a second image reconstructing section that performs image reconstruction processing with respect to the second collection data weighted by the collection data processing section to generate second intermediate image data, and a combining section that combines the first intermediate image data with the second intermediate image data to generate the complete image data.

2. The X-ray CT scanner according to claim 1, wherein the plurality of X-ray tubes are arranged in such a manner that angles formed between X-ray irradiation directions adjacent to each other on a rotation plane become uneven.

3. The X-ray CT scanner according to claim 1, wherein the plurality of X-ray tubes include:

a third X-ray tube having a third fan angle that is substantially the same as the first fan angle, and the collection data processing section is configured to execute the weighting processing with respect to the first collection data, the second collection data, and third collection data obtained by the third X-ray detector arranged to face the third X-ray tube.

4. The X-ray CT scanner according to claim 1, further comprising:

a display processing section that displays a boundary between a plurality of different imaging fields of view formed based on the different fan angles.

5. The X-ray CT scanner according to claim 1, further comprising:

a display processing section that enlarges image data in a minimum imaging field of view generated by the first image generating section in the plurality of different imaging fields of view formed based on the different fan angles to a different imaging field of view size; and a display device that displays the image data enlarged by the display processing section.

6. The X-ray CT scanner according to claim 1, further comprising:

a second image generating section that reconstructs data from a single X-ray detector in the plurality of X-ray detectors to generate image data; and a display processing section that switches and displays the image data generated by the first image generating section and the image data generated by the second image generating section.

7. A data processing method of an X-ray CT scanner, comprising:

a first step of acquiring a plurality of pieces of collection data including first collection data and second collection data which are respectively emitted from a plurality of X-ray tubes including a first X-ray tube having a first fan angle and a second X-ray tube having a second fan angle larger than the first fan angle and respectively obtained by a first X-ray detector and a second X-ray detector which are respectively arranged to face the first X-ray tube and the second X-ray tube and have detection elements;

a second step of cutting out and omitting from the plurality of pieces of collection data, pieces of (1) data simultaneously collected by the first X-ray detector and the second X-ray detector from a first imaging field of view covered by the first X-ray detector in accordance with each segment and (2) data collected by the second X-ray detector from a region in a second field of view covered by the second X-ray detector outside the first imaging field of view so that the first and second collection data each have respective defective portions corresponding to regions outside the respective imaging fields of view of the first and second X-ray tubes, and executing weighting processing with respect to each of the plurality of remaining pieces of collection data to generate weighted first and second collection data smoothed in a direction corresponding to a channel direction of the detection elements in the first X-ray detector and the second X-ray detector; and a third step of performing processing including image reconstruction processing with respect to the plurality of pieces of weighted collection data to generate the image data, comprising, performing image first reconstruction processing with respect to the first weighted collection data to generate first intermediate image data;

performs image second reconstruction processing with respect to the second weighted collection data to generate second intermediate image data; and combining the first intermediate image data with the second intermediate image data to generate the complete image data.

8. The X-ray CT scanner according to claim 1, wherein a data collection period and a view angle for the first collection data are less than a data collection period and a view angle for the second collection data.

* * * * *